(12) United States Patent
Dunkel et al.

(10) Patent No.: US 7,470,793 B2
(45) Date of Patent: Dec. 30, 2008

(54) THIAZOL-(BI)CYCLOALKYL-CARBOXANILIDES

(75) Inventors: Ralf Dunkel, Monheim (DE); Heiko Rieck, Foy les Lyon (FR); Hans-Ludwig Elbe, Wuppertal (DE); Jörg Nico Greul, Leichlingen (DE); Ulrike Wachendorff-Neumann, Neuwied (DE); Karl-Heinz Kuck, Langenfeld (DE); Peter Dahmen, Neuss (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/532,529

(22) PCT Filed: Oct. 15, 2003

(86) PCT No.: PCT/EP03/11392

§ 371 (c)(1),
(2), (4) Date: Aug. 23, 2005

(87) PCT Pub. No.: WO2004/039789

PCT Pub. Date: May 13, 2004

(65) Prior Publication Data

US 2006/0155122 A1    Jul. 13, 2006

(30) Foreign Application Priority Data

Oct. 28, 2002    (DE) ................. 102 50 110

(51) Int. Cl.
 *C07D 417/02* (2006.01)
(52) U.S. Cl. ...................... 548/181; 548/200
(58) Field of Classification Search ............... 548/181, 548/200
 See application file for complete search history.

(56) References Cited

U.S. PATENT DOCUMENTS

| | | | | |
|---|---|---|---|---|
| 4,914,097 A | | 4/1990 | Oda et al. .................. 514/255 |
| 4,956,375 A | | 9/1990 | Oda et al. .................. 514/261 |
| 5,330,995 A | * | 7/1994 | Eicken et al. .............. 514/355 |
| 5,416,103 A | | 5/1995 | Eicken et al. .............. 514/355 |
| 5,438,070 A | | 8/1995 | Eicken et al. .............. 514/403 |
| 5,480,897 A | * | 1/1996 | Eicken et al. .............. 514/365 |
| 5,521,317 A | | 5/1996 | Briner ....................... 548/200 |
| 5,556,988 A | * | 9/1996 | Eicken et al. ............. 548/374.1 |
| 5,589,493 A | * | 12/1996 | Eicken et al. .............. 514/355 |
| 5,728,869 A | | 3/1998 | Briner ........................ 562/452 |
| 5,998,450 A | * | 12/1999 | Eicken et al. .............. 514/355 |
| 6,346,538 B1 | * | 2/2002 | Schelberger et al. ........ 514/312 |
| 6,350,765 B1 | * | 2/2002 | Schelberger et al. ........ 514/355 |
| 6,365,608 B1 | * | 4/2002 | Schelberger et al. ........ 514/352 |
| 6,372,748 B1 | * | 4/2002 | Schelberger et al. ........ 514/256 |
| 6,410,572 B1 | * | 6/2002 | Schelberger et al. ........ 514/355 |
| 6,489,348 B1 | * | 12/2002 | Schelberger et al. ........ 514/355 |
| 6,569,875 B1 | * | 5/2003 | Schelberger et al. ........ 514/355 |
| 6,903,108 B2 | * | 6/2005 | Schelberger et al. ........ 514/275 |

FOREIGN PATENT DOCUMENTS

| | | | |
|---|---|---|---|
| EP | 0 276 177 | | 7/1988 |
| EP | 0 315 502 | | 5/1989 |
| EP | 0 371 950 | | 6/1990 |
| EP | 0 591 699 | | 4/1994 |
| WO | WO9931984 | * | 7/1999 |
| WO | 02/08917 | | 1/2002 |
| WO | 02/059086 | | 8/2002 |
| WO | 03/066610 | | 8/2003 |
| WO | 03/074491 | | 9/2003 |
| WO | WO 03074491 A1 | * | 9/2003 |

OTHER PUBLICATIONS

Patani et al, Bioisosterism: A Rational Approach in Drug Design, 1996, 96, 3147-3150.*

* cited by examiner

*Primary Examiner*—Kamal A Saeed
(74) *Attorney, Agent, or Firm*—Raymond J. Harmuth; Richard E. L. Henderson

(57) ABSTRACT

This invention relates to novel thiazole(bi)cycloalkylcarboxanilides of the formula (I)

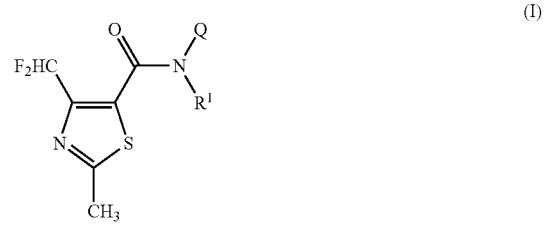

in which Q and $R^1$ are as defined in the disclosure, to a process for preparing these compounds and to their use for controlling unwanted microorganisms.

8 Claims, No Drawings

THIAZOL-(BI)CYCLOALKYL-CARBOXANILIDES

The present patent application has been filed under 35 U.S.C. 371 as a national stage application of PCT/EP2003/011392, filed Oct. 15, 2003, which was published in German as International Patent Publication WO 2004/039789 on Mar. 13, 2004, and is entitled to the right of priority of German Patent Application 102 50 110.6, filed Oct. 28, 2002.

The present invention relates to novel thiazole(bi)cycloalkylcarboxanilides, to a plurality of processes for their preparation and to their use for controlling unwanted microorganisms.

It is already known that numerous thiazole(bi)cycloalkyl-carboxanilides have fungicidal properties (cf., for example, WO 02/059086, EP-A 0 591 699, EP-A 0 589 301, EP-A 0 545 099, EP-A 0 315 502 and EP-A 0 276 177). Thus, for example, the following thiazole(bi)cycloalkylcarboxanilides are already known: 2-amino-N-(2-cyclohexylphenyl)-4-(trifluoromethyl)-1,3-thiazole-5-carboxamide and 2-amino-N-(2-cyclopentylphenyl)-4-(trifluoromethyl)-1,3-thiazole-5-carboxamide from EP-A 0 589 301, N-(2-cyclohexylphenyl)-2-methyl-4-(trifluoromethyl)-1,3-thiazole-5-carboxamide and N-(2-cyclopentylphenyl)-2-methyl-4-(trifluoromethyl)-1,3-thiazole-5-carboxamide from EP-A 0 545 099, 2-methyl-4-(trifluoromethyl)-N-(1,1,3-trimethyl-2,3-dihydro-1H-inden-4-yl)-1,3-thiazole-5-carboxamide from EP-A 0 276 177 and 2-methyl-4-(trifluoromethyl)-N-(1,1,3-trimethyl-1,3-dihydro-2-benzofuran-4-yl)-1,3-thiazole-5-carboxamide from EP-A 0 315 502. The activity of these compounds is good; however, in some cases, for example at low application rates, it is unsatisfactory.

This invention now provides novel thiazole(bi)cycloalkylcarboxanilides of the formula (I)

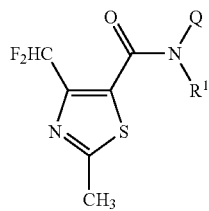

(I)

in which
Q represents a group

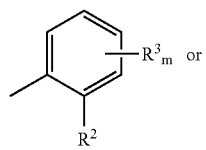

(Q-1)

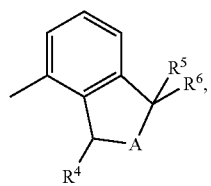

(Q-2)

$R^1$ represents hydrogen, $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^7$, —$CONR^8R^9$ or —$CH_2NR^{10}R^{11}$, $R^2$ represents $C_3$-$C_{12}$-cycloalkyl, $C_3$-$C_{12}$-cycloalkenyl, $C_6$-$C_{12}$-bicycloalkyl or $C_6$-$C_{12}$-bicycloalkenyl, each of which is optionally mono- or polysubstituted by identical or different substituents from the group consisting of halogen, cyano, hydroxyl, $C_1$-$C_8$-alkyl, $C_1$-$C_8$-alkoxy, $C_1$-$C_6$-haloalkyl, $C_1$-$C_6$-haloalkoxy having in each case 1 to 9 fluorine, chlorine and/or bromine atoms, $R^3$ represents fluorine, chlorine, bromine or methyl, m represents 0, 1, 2, 3 or 4, A represents O (oxygen) or $CR^{12}$, $R^4$, $R^5$, $R^6$ and $R^{12}$ independently of one another represent hydrogen, methyl or ethyl, $R^7$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms or 4-(difluoromethyl)-2-methyl-1,3-thiazol-2-yl, $R^8$ and $R^9$ independently of one another represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^8$ and $R^9$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further nonadjacent heteroatoms from the group consisting of oxygen, sulfur and $NR^{13}$, $R^{10}$ and $R^{11}$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^{10}$ and $R^{11}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further nonadjacent heteroatoms from the group consisting of oxygen, sulfur and $NR^{13}$, $R^{13}$ represents hydrogen or $C_1$-$C_6$-alkyl.

Furthermore, it has been found that thiazole(bi)cycloalkylcarboxanilides of the formula (I) are obtained when A) carboxylic acid derivatives of the formula (II)

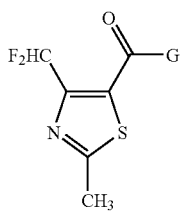

(II)

in which
G represents halogen, hydroxyl or $C_1$-$C_6$-alkoxy,
are, in a first step, reacted with aniline derivatives of the formula (III)

$$H_2N-Q \quad (III)$$

in which
Q is as defined above
in the presence of an acid binder and in the presence of a diluent
and the resulting products of the formula (I-a)

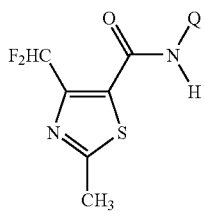

in which
Q is as defined above
are, if appropriate, reacted in a second step with a halide of the formula (III)

$$R^{1-1}-X \quad (IV)$$

in which
$R^{1-1}$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^7$, —$CONR^8R^9$ or —$CH_2NR^{10}R^{11}$,
$R^7$, $R^8$, $R^9$, $R^{10}$ and $R^{11}$ are as defined above and
X represents chlorine, bromine or iodine,
in the presence of a base and in the presence of a diluent.
Finally, it has been found that the novel thiazole(bi)cycloalkylcarboxanilides of the formula (I) have very good microbicidal properties and can be used for controlling unwanted micro-organisms both in crop protection and in the protection of materials.
Surprisingly, the thiazole(bi)cycloalkylcarboxanilides of the formula (I) according to the invention have considerably better fungicidal activity than the constitutionally most similar active compounds of the prior art having the same direction of action.
The formula (I) provides a general definition of the thiazole (bi)cycloalkylcarboxanilides according to the invention. Preferred substituents or ranges of the radicals listed in the formulae mentioned above and below are illustrated below.
$R^1$ preferably represents hydrogen; $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms; —$COR^7$, —$CONR^8R^9$ or —$CH_2NR^{10}R^{11}$.
$R^1$ particularly preferably represents hydrogen, methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, trifluoromethoxymethyl; —$COR^7$, —$CONR^8R^9$ or —$CH_2NR^{10}R^{11}$.
$R^1$ very particularly preferably represents hydrogen; methyl, methoxymethyl or —$COR^7$.
$R^2$ preferably represents $C_3$-$C_{12}$-cycloalkyl, $C_3$-$C_{12}$-cycloalkyl, $C_3$-$C_{12}$-cycloalkenyl, $C_6$-$C_{12}$-bicycloalkyl or $C_6$-$C_{12}$-bicycloalkenyl, each of which is optionally mono- to tetrasubstituted by identical or different substituents from the group consisting of fluorine, chlorine, bromine, cyano, hydroxyl, $C_1$-$C_6$-alkyl, $C_1$-$C_6$-alkoxy, $C_1$-$C_4$-haloalkyl, $C_1$-$C_4$-haloalkoxy having in each case 1 to 9 fluorine, chlorine and/or bromine atoms.
$R^2$ particularly preferably represents $C_3$-$C_{10}$-cycloalkyl, $C_3$-$C_{10}$-cycloalkenyl, $C_6$-$C_{10}$-bicycloalkyl or $C_6$-$C_{10}$-bicycloalkenyl, each of which is optionally mono- to trisubstituted by identical or different substituents from the group consisting of fluorine, chlorine, bromine, cyano, hydroxyl, methyl, ethyl, n- or isopropyl, n-, iso-, sec- or tert-butyl, methoxy, ethoxy, n- or isopropoxy, n-, iso-, sec- or tert-butoxy, trifluoromethyl, difluoromethyl, trichloromethyl, difluorochloromethyl, trifluoromethoxy, difluoromethoxy, trichloromethoxy, difluorochloromethoxy.
$R^2$ very particularly preferably represents cyclopropyl, cyclopentyl, cyclohexyl, cyclopentyl, cyclohexyl, cycloheptyl, cyclooctyl, cyclohexenyl, cycloheptenyl, cyclooctenyl, bicyclo[4.1.0]heptyl, bicyclo[2.2.1]heptyl, each of which is mono- to trisubstituted by identical or different substituents from the group consisting of fluorine, chlorine, bromine, methyl, ethyl, isopropyl, tert-butyl, methoxy, ethoxy, isopropoxy, tert-butoxy, trifluoromethyl, trifluoromethoxy.
$R^3$ preferably represents fluorine, bromine or methyl.
$R^3$ particularly preferably represents fluorine or methyl.
m preferably represents 0, 1, 2 or 3.
m particularly preferably represents 0, 1 or 2.
A preferably represents O (oxygen).
A preferably represents $CR^{12}$.
$R^4$ preferably represents methyl or ethyl.
$R^4$ particularly preferably represents methyl.
$R^5$ and $R^6$ preferably each represent methyl.
$R^7$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms or 4-(difluoromethyl)-2-methyl-1,3-thiazol-2-yl.
$R^7$ particularly preferably represents hydrogen, methyl, ethyl, n- or isopropyl, tert-butyl, methoxy, ethoxy, tert-butoxy, cyclopropyl; trifluoromethyl, trifluoromethoxy or 4-(difluoromethyl)-2-methyl-1,3-thiazol-2-yl.
$R^7$ very particularly preferably represents hydrogen or 4-(difluoromethyl)-2-methyl-1,3-thiazol-2-yl.
$R^8$ and $R^9$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.
$R^8$ and $R^9$ furthermore together with the nitrogen atom to which they are attached preferably form a saturated heterocycle which is optionally mono- to tetrasubstituted by identical or different substituents from the group consisting of halogen and $C_1$-$C_4$-alkyl and which has 5 to 8 ring atoms, where the heterocycle may contain 1 or 2 further nonadjacent heteroatoms from the group consisting of oxygen, sulfur and $NR^{13}$.

$R^8$ and $R^9$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^8$ and $R^9$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^{13}$.

$R^{10}$ and $R^{11}$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^{10}$ and $R^{11}$ furthermore together with the nitrogen atom to which they are attached preferably form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further nonadjacent heteroatoms from the group consisting of oxygen, sulfur and $NR^{13}$.

$R^{10}$ and $R^{11}$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^{10}$ and $R^{11}$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^{13}$.

$R^{12}$ preferably represents hydrogen or methyl.

$R^{12}$ particularly preferably represents hydrogen.

$R^{13}$ preferably represents hydrogen or $C_1$-$C_4$-alkyl.

$R^{13}$ particularly preferably represents hydrogen, methyl, ethyl, n- or isopropyl, n-, iso-, sec- or tert-butyl.

Furthermore preferred are thiazole(bi)cycloalkylcarboxanilides of the formula (I) in which $R^1$ represents hydrogen.

Furthermore preferred are thiazole(bi)cycloalkylcarboxanilides of the formula (I) in which $R^1$ represents methyl.

Furthermore preferred are thiazole(bi)cycloalkylcarboxanilides of the formula (I) in which $R^1$ represents —CHO.

Furthermore preferred are thiazole(bi)cycloalkylcarboxanilides of the formula (I) in which $R^1$ represents methylcarbonyl (acetyl).

Furthermore preferred are thiazole(bi)cycloalkylcarboxanilides of the formula (I) in which Q represents Q-1 and $R^2$ represents bicyclo[2.2.1]heptyl (norbornanyl).

Furthermore preferred are thiazole(bi)cycloalkylcarboxanilides of the formula (I) in which Q represents Q-1 and m represents 0.

Furthermore preferred are thiazole(bi)cycloalkylcarboxanilides of the formula (I) in which Q represents Q-1, m represents 1 and $R^3$ represents fluorine or methyl.

Moreover, preference is given to thiazole(bi)cycloalkylcarboxanilides of the formula (I-a)

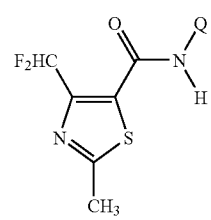

(I-a)

in which
Q is as defined above.

Moreover, preference is given to thiazole(bi)cycloalkylcarboxanilides of the formula (I-b)

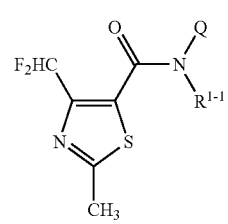

(I-b)

in which
Q is as defined above, $R^{1-1}$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^7$, —$CONR^8R^9$ or —$CH_2NR^{10}R^{11}$, $R^7$, $R^8$, $R^9$, $R^{10}$ and $R^{11}$ are as defined above.

$R^{1-1}$ preferably represents $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms; —$COR^7$, —$CONR^8R^9$ or —$CH_2NR^{10}R^{11}$.

$R^{1-1}$ particularly preferably represents methyl, ethyl, n- or isopropyl, n-, iso-, sec- or tertbutyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, trifluoromethoxymethyl; —$COR^7$, —$CONR^8R^9$ or —$CH_2NR^{10}R^{11}$.

$R^{1-1}$ very particularly preferably represents methyl or —$COR^7$.

Moreover, preference is given to thiazole(bi)cycloalkylcarboxanilides of the formula (I-c)

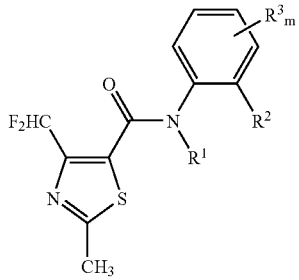

(I-c)

in which
$R^1$, $R^2$ and $R^3$ are as defined above.

Moreover, preference is given to thiazole(bi)cycloalkylcarboxanilides of the formula (I-d)

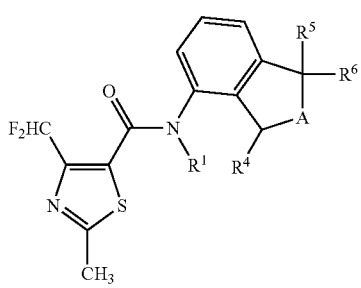

(I-d)

in which
A, $R^4$, $R^5$ and $R^6$ are as defined.

The preferred, particularly preferred and very particularly preferred definitions of the respective radicals $R^1$ to $R^3$, Q, m and A apply correspondingly to the compounds of the formulae (I-a), (I-b), (I-c) and (I-d).

Saturated or unsaturated hydrocarbon radicals, such as alkyl and alkenyl, can in each case be straight-chain or branched as far as this is possible, including in combination with heteroatoms, such as, for example, an alkoxy.

Optionally substituted radicals can be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the general or preferred radical definitions or illustrations given above can also be combined with one another as desired, i.e. between the respective ranges and preferred ranges. They apply both to the end products and, correspondingly, to the precursors and intermediates. Moreover, individual definitions may not apply.

Using 4-(difluoromethyl)-2-methyl-1,3-thiazole-5-carbonyl chloride and 2-bicyclo[2.2.1]hept-2-ylaniline as starting materials in the first step and additionally acetyl chloride as starting material in the second step, the course of the process A) according to the invention can be illustrated by the formula scheme below.

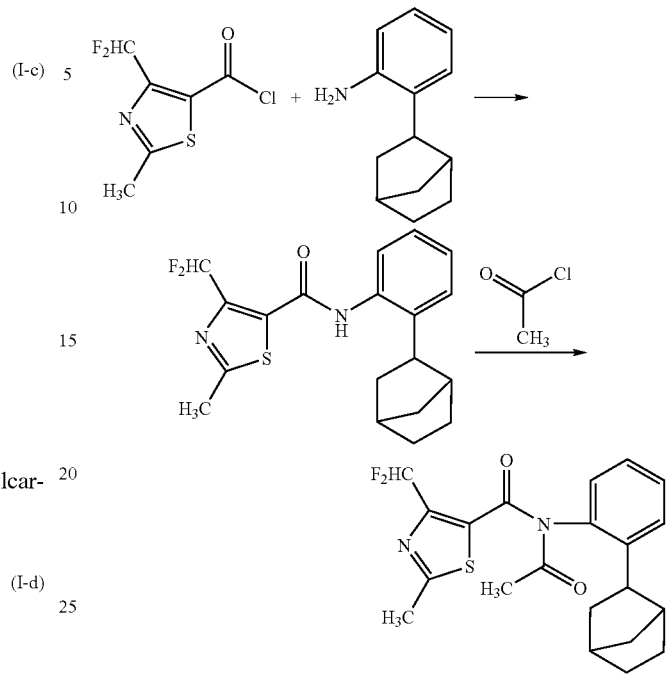

Illustration of the Processes and Intermediates

The formula (II) provides a general definition of the carboxylic acid derivatives required as starting materials for carrying out the first step of the process A) according to the invention. In this formula, G preferably represents chlorine, bromine, hydroxyl, methoxy or ethoxy, particularly preferably chlorine, hydroxyl or methoxy, very particularly preferably chlorine.

The carboxylic acid derivatives of the formula (II) are known or can be prepared by known processes (cf. EP-A 0 545 099 and EP-A 0 589 313).

The formula (III) provides a general definition of the aniline derivatives required as reaction components for carrying out the first step of the process A) according to the invention. In this formula, Q preferably has one of the meanings Q-1 and Q-2.

The aniline derivatives of the formula (III) are known, and/or some of them can be prepared by known methods (cf. EP-A 0 545 099 and EP-A 0 589 301 for Q-1, EP-A 0 654 464, EP-A 0 315 502 and EP-A 0 280 275 for Q-2).

The compounds of the formula (I-a) used as reaction components for carrying out step two of the process A) according to the invention are a subgroup of the thiazole(bi)cycloalkylcarboxanilides of the formula (I) according to the invention and thus also form part of the subject-matter of the present application.

The formula (IV) provides a general definition of the halides required as reaction components for carrying out the second step of the process A) according to the invention. In this formula, Q preferably has one of the meanings Q-1 and Q-2. $R^{1-1}$ preferably, particularly preferably and very particularly preferably has those meanings which have already been given in connection with the description of the compounds of the formula (I-b) according to the invention as being preferred, particularly preferred and very particularly preferred, respectively, for these radicals. X is preferably chlorine or bromine.

Halides of the formula (III) are known chemicals for synthesis.

Suitable acid binders for carrying out the first step of the process A) according to the invention are all inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylamino-pyridine, diazabicyclooctane (DABCO), diazabicyclononene (DBN) or diazabicycloundecene (DBU). However, it is also possible to operate without additional acid binder or to use an excess of the amine component so that it simultaneously acts as acid binder.

Suitable diluents for carrying out the first step of the process A) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide, or sulfones, such as sulfolan.

When carrying out the first step of the process A) according to the invention, the reaction temperatures can in each case be varied within a relatively wide range. In general, the reaction is carried out at temperatures between 0° C. and 140° C., preferably between 10° C. and 120° C.

When carrying out the first step of the process A) according to the invention, the reaction is generally in each case carried out under atmospheric pressure. However, in each case it is also possible to operate under elevated or reduced pressure.

When carrying out the first step of the process A) according to the invention, in general 1 mol or else an excess of aniline derivative of the formula (III) and from 1 to 3 mol of acid binder are employed per mole of carboxylic acid derivative of the formula (II). However, it is also possible to employ the reaction components in other ratios. Work-up is carried out by customary methods. In general, water is added to the reaction mixture and the organic phase is separated off and, after drying, concentrated under reduced pressure. The residue that remains may, if appropriate, be freed from any impurities that may still be present using customary methods, such as chromatography or recrystallization.

Suitable diluents for carrying out the second step of the process A) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide The second step of the process A) according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the second step of the process A) according to the invention, the reaction temperatures can be varied within a relatively wide range. In general, the reaction is carried out at temperatures of from 0° C. to 150° C., preferably at temperatures of from 20° C. to 110° C.

When carrying out the second step of the process A) according to the invention, the reaction is generally in each case carried out under atmospheric pressure. However, in each case it is also possible to operate under elevated or reduced pressure.

For carrying out the second step of the process (A) for preparing the compounds of the formula (I), in general from 0.2 to 5 mol, preferably from 0.5 to 2 mol, of the halide of the formula (III) are employed per mole of the thiazolylbiphenylamide of the formula (II).

The compounds according to the invention have potent microbicidal activity and can be employed for controlling unwanted microorganisms, such as fungi and bacteria, in crop protection and in the protection of materials.

Fungicides can be employed crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

*Sphaerotheca* species, such as, for example, *Sphaerotheca fuliginea;*
*Podosphaera* species, such as, for example, *Podosphaera leucotricha;*
*Venturia* species, such as, for example, *Venturia inaequalis;*
*Pyrenophora* species, such as, for example, *Pyrenophora teres* or *P. graminea* (conidia form: *Drechslera,* syn: *Helminthosporium*);
*Cochliobolus* species, such as, for example, *Cochliobolus sativus* (conidia form: *Drechslera,* syn: *Helminthosporium*);
*Uromyces* species, such as, for example, *Uromyces appendiculatus;*
*Puccinia* species, such as, for example, *Puccinia recondita;*
*Sclerotinia* species, such as, for example, *Sclerotinia sclerotiorum;*
*Tilletia* species, such as, for example, *Tilletia caries;*
*Ustilago* species, such as, for example, *Ustilago nuda* or *Ustilago avenae;*
*Pellicularia* species, such as, for example, *Pellicularia sasakii;*
*Pyricularia* species, such as, for example, *Pyricularia oryzae;*
*Fusarium* species, such as, for example, *Fusarium culmorum;*
*Botrytis* species, such as, for example, *Botrytis cinerea;*
*Septoria* species, such as, for example, *Septoria nodorum;*
*Leptosphaeria* species, such as, for example, *Leptosphaeria nodorum;*
*Cercospora* species, such as, for example, *Cercospora canescens;*
*Alternaria* species, such as, for example, *Alternaria brassicae;* and
*Pseudocercosporella* species, such as, for example, *Pseudocercosporella herpotrichoides.*

The active compounds according to the invention also show a strong invigorating action in plants. Accordingly, they are suitable for mobilizing the internal defenses of the plant against attack by unwanted microorganisms.

In the present context, plant-invigorating (resistance-inducing) compounds are to be understood as meaning substances which are capable of stimulating the defense system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, papers and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes) and against slime organisms and algae.

Microorganisms of the following genera may be mentioned as examples:
*Alternaria,* such as *Alternaria tenuis,*
*Aspergillus,* such as *Aspergillus niger,*
*Chaetomium,* such as *Chaetomium globosum,*
*Coniophora,* such as *Coniophora puetana,*
*Lentinus,* such as *Lentinus tigrinus,*
*Penicillium,* such as *Penicillium glaucum,*
*Polyporus,* such as *Polyporus versicolor,*
*Aureobasidium,* such as *Aureobasidium pullulans,*
*Sclerophoma,* such as *Sclerophoma pityophila,*
*Trichoderma,* such as *Trichoderma viride,*
*Escherichia,* such as *Escherichia coli,*
*Pseudomonas,* such as *Pseudomonas aeruginosa,* and
*Staphylococcus,* such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolyzates. Suitable dispersants are: for example lignosulfite waste liquors and methylcellulose.

Tackifiers such as carboxymethylcellulose, natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:
2-phenylphenol; 8-hydroxyquinoline sulfate;
acibenzolar-S-methyl; aldimorph; amidoflumet; ampropylfos; ampropylfos-potassium; andoprim; anilazine; azaconazole; azoxystrobin;
benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine;
calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;
Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;
edifenphos; epoxiconazole; ethaboxam; ethirimol; etridiazole;
famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox;
guazatine; hexachlorobenzene; hexaconazole; hymexazole;
imazalil; imibenconazole; iminoctadine triacetate; iminoctadine tris(albesil); iodocarb; ipconazole; iprobenfos; iprodione; iprovalicarb; irumamycin; isoprothiolane; isovaledione;
kasugamycin; kresoxim-methyl;
mancozeb; maneb; meferimzone; mepanipyrim; mepronil; metalaxyl; metalaxyl-M; metconazole; methasulfocarb; methfturoxam; metiram; metominostrobin; metsulfovax; mildiomycin; myclobutanil; myclozolin;
natamycin; nicobifen; nitrothal-isopropyl; noviflumuron; nuarimol;
ofurace; orysastrobin; oxadixyl; oxolinic acid; oxpoconazole; oxycarboxin; oxyfenthiin;
paclobutrazole; pefurazoate; penconazole; pencycuron; phosdiphen; phthalide; picoxy-strobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine;
quinconazole; quinoxyfen; quintozene; simeconazole; spiroxamine; sulfur;
tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;
uniconazole; validamycin A; vinclozolin; zineb; ziram; zoxamide;
(2S)-N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5- dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1, 2,4-triazol-1-yl)cycloheptanol; methyl 1-(2,3-dihydro-2, 2-dimethyl-1H-inden-1-yl)-1H-imidazole-5-carboxylate; monopotassium carbonate; N-(6-methoxy3-pyridinyl)cyclopropanecarboxamide;

N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; copper oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), armidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorbenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methyl-sulfone, diafenthiuron, dialifos, diazinon, dichlofenthion, dichlorvos, dicofol, dicrotophos, dicyclanil, diflubenzuron, di-methoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, ometoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphosmethyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii,*

WL-108477, WL-40027, YI-5201, YI-5301, YI-5302, XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO 96/37494, WO 98/25923), and preparations which comprise insecticidally active plant extracts, nematodes, fungi or viruses.

A mixture with other known active compounds, such as herbicides, or with fertilizers and growth regulators is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidal active compounds. Examples of transgenic plants which may be mentioned are the important crop plants, such as cereals (wheat, rice), maize, soybeans, potatoes, cotton, tobacco, oilseed rape and also fruit plants (with the fruits apples, pears, citrus fruits and grapes), and particular emphasis is given to maize, soybeans, potatoes, cotton, tobacco and oilseed rape.

Traits that are emphasized are in particular increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulfonylureas, glyphosates or phosphinotricin (for example the "PAT" gene). The genes which impart the desired traits in question can also be present in combination with one another in the transgenic plants. Examples of "Bt plants" which may be mentioned are maize varieties, cotton varieties, soybean varieties and potato varieties which are sold under the trade names YIELD GARD® (for example maize, cotton, soybeans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soybean varieties which are sold under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

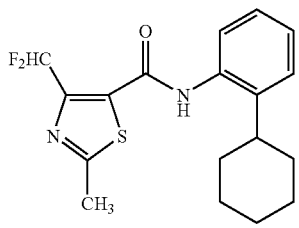

2-Cyclohexylaniline (175 mg, 1 mmol) and 4-(difluoromethyl)-2-methyl-1,3-thiazole-5-carbonyl chloride (212 mg, 1.2 mmol) are added dropwise to a suspension of potassium carbonate (138 mg) in acetonitrile (30 ml). The reaction mixture is stirred for 10 hours. For work-up, water (30 ml) is added to the reaction mixture, which is then extracted with ethyl acetate. The organic phase is dried using magnesium sulfate, filtered and concentrated. The residue is purified on silica gel (gradient cyclohexane/ethyl acetate 100:0→20:80).

This gives 210 mg (57%) of N-(2-cyclohexylphenyl)-4-(difluoromethyl)-2-methyl-1,3-thiazole-5-carboxamide of logP (pH 2.3)=3.50.

Example 2

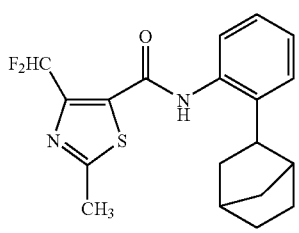

2-Bicyclo[2.2.1]hept-2-ylaniline (562 mg, 3 mmol) and 4-(difluoromethyl)-2-methyl-1,3-thiazole-5-carbonyl chloride (635 mg, 3.6 mmol) are added dropwise to a suspension of potassium carbonate (415 mg) in acetonitrile (30 ml). The reaction mixture is stirred for 10 hours.

For work-up, water (30 ml) is added to the reaction mixture, which is then extracted with ethyl acetate. The organic phase is dried using magnesium sulfate, filtered and concentrated. The residue is purified on silica gel (gradient cyclohexane/ethyl acetate 100:0→20:80).

This gave 150 mg (13%) of N-(2-bicyclo[2.2.1]hept-2-ylphenyl)-4-(difluoromethyl)-2-methyl-1,3-thiazole-5-carboxamide of logP (pH 2.3)=3.63.

The compounds listed in Table 1 below are likewise prepared analogously to Examples 1 and 2 and analogously to the general descriptions of the processes.

TABLE 1

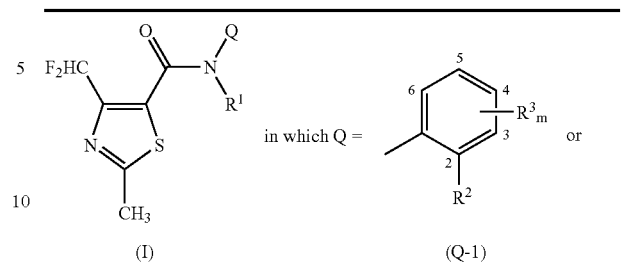

| Ex. | Q | $R^1$ | $R^2$ | $R^3_m$ | logP (pH 2.3) |
|---|---|---|---|---|---|
| 3 | Q-1 | H | bicyclo[2.2.1]hept-2-yl | 4-$CH_3$ | 3.92 |
| 4 | Q-1 | H | bicyclo[2.2.1]hept-2-yl | 5-$CH_3$ | 4.00 |
| 5 | Q-1 | H | cycloheptyl | 4-F | 3.84 |
| 6 | Q-1 | H | cyclopentyl | 4-F | 3.24 |
| 7 | Q-2-a | H | — | — | 3.62 |
| 8 | Q-1 | H | cyclooctyl | — | 4.06 |
| 9 | Q-1 | H | cyclooctyl | 4-$CH_3$ | 4.43 |
| 10 | Q-1 | H | cyclopentyl | 4,5-$(CH_3)_2$ | 3.78 |
| 11 | Q-1 | H | cyclooctyl | 4-F | 4.10 |
| 12 | Q-1 | H | cyclooctyl | 5-$CH_3$ | 4.44 |
| 13 | Q-1 | H | cyclooctyl | 5-F | 4.10 |
| 14 | Q-1 | H | bicyclo[2.2.1]hept-2-yl | 4-Br | 4.27 |
| 15 | Q-1 | H | bicyclo[2.2.1]hept-2-yl | 4,5-$(CH_3)_2$ | 4.22 |
| 16 | Q-1 | H | cyclopentyl | — | 3.19 |
| 17 | Q-1 | H | 4-methylcyclohexyl | — | 3.82 |
| 18 | Q-1 | H | (3R)-3-methylcyclohexyl | — | 3.88 |
| 19 | Q-1 | $CH_3$ | bicyclo[2.2.1]hept-2-yl | — | 3.96 |
| 20 | Q-1 | $CH_3$ | cyclohexyl | — | 3.85 |
| 21 | Q-1 | $COCH_3$ | bicyclo[2.2.1]hept-2-yl | — | 3.95 |
| 22 | Q-1 | $COCH_3$ | cyclohexyl | — | 3.86 |
| 23 | Q-1 | H | 2-cyclohepten-1-yl | 4-F | 3.68 |
| 24 | Q-1 | H | cycloheptyl | — | 3.81 |

The logP values given in the Preparation Examples were determined in accordance with EEC directive 79/831 Annex V.A8 by HPLC (High Performance Liquid Chromatography) on a reversed-phase column (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Sphaerotheca* Test (Cucumber)/Protective
Solvents: 24.5 parts by weight of acetone
  24.5 parts by weight of N,N-dimethylacetamide
Emulsifier: 1 part by weight of alkylaryl polyglycol ether
  To produce a suitable preparation of active compound, 1 part by weight of active compound is mixed with the stated amounts of solvents and emulsifier, and the concentrate is diluted with water to the desired concentration.

To test for protective activity, young cucumber plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE A

*Sphaerotheca* test (cucumber)/protective

| Active compound | | Active compound application rate in g/ha | Efficacy in % |
|---|---|---|---|
| 6 | [structure: F₂HC-thiazole-C(O)NH-(4-F-2-cyclopentyl-phenyl), H₃C on thiazole] | 100 | 88 |
| 8 | [structure: F₂HC-thiazole-C(O)NH-(2-cyclooctyl-phenyl), H₃C on thiazole] | 100 | 93 |
| 14 | [structure: F₂HC-thiazole-C(O)NH-(4-Br-2-bicycloheptyl-phenyl), H₃C on thiazole] | 100 | 100 |
| 18 | [structure: F₂HC-thiazole-C(O)NH-(2-(4-methylcyclohexyl)-phenyl), H₃C on thiazole] | 100 | 100 |
| 19 | [structure: F₂HC-thiazole-C(O)N(CH₃)-(2-bicycloheptyl-phenyl), H₃C on thiazole] | 100 | 98 |
| 20 | [structure: F₂HC-thiazole-C(O)N(CH₃)-(2-cyclohexyl-phenyl), H₃C on thiazole] | 100 | 100 |
| 21 | [structure: F₂HC-thiazole-C(O)N(C(O)CH₃)-(2-bicycloheptyl-phenyl), H₃C on thiazole] | 100 | 98 |
| 22 | [structure: F₂HC-thiazole-C(O)N(C(O)CH₃)-(2-cyclohexyl-phenyl), H₃C on thiazole] | 100 | 96 |
| 2 | [structure: F₂HC-thiazole-C(O)NH-(2-bicycloheptyl-phenyl), H₃C on thiazole] | 100 | 100 |
| 1 | [structure: F₂HC-thiazole-C(O)NH-(2-cyclohexyl-phenyl), H₃C on thiazole] | 100 | 89 |

Example B

*Venturia* Test (Apple)/Protective

Solvents: 2.5 parts by weight of acetone
24.5 parts by weight of dimethylacetamide Emulsifier: 1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabinet at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

*Venturia* test (apple)/protective

| Active compound | Active compound application rate in g/ha | Efficacy in % |
|---|---|---|
| 6 | 100 | 99 |
| 7 | 100 | 100 |
| 8 | 100 | 100 |
| 14 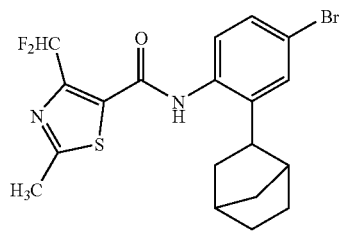 | 100 | 100 |
| 16 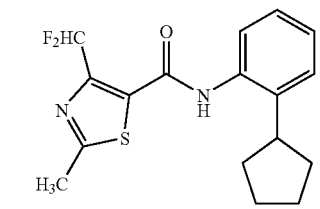 | 100 | 99 |
| 18 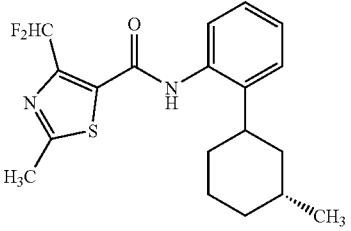 | 100 | 100 |
| 21 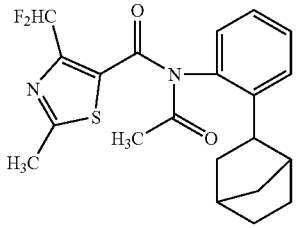 | 100 | 96 |
| 2 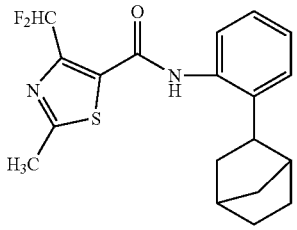 | 100 | 100 |
| 1 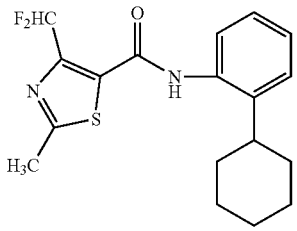 | 100 | 100 |

Example C

*Puccinia* Test (Wheat)/Protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at about 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

*Puccinia* test (wheat)/protective

| Active compound | Active compound application rate in g/ha | Efficacy in % |
|---|---|---|
| 7 (structure) | 500 | 100 |
| 8 (structure) | 500 | 100 |
| 22 (structure) | 500 | 93 |
| 2 (structure) | 500 | 100 |
| 1 (structure) | 500 | 100 |

Example D

*Alternaria* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani*. The plants then remain at 100% relative atmospheric humidity and 20° C. for 24 hours. Subsequently, the plants remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

*Alternaria* test (tomato)/protective

| Active compound | Active compound application rate in g/ha | Efficacy in % |
|---|---|---|
| 7 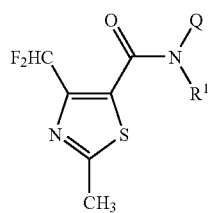 | 750 | 100 |
| 14 | 750 | 95 |
| 18 | 750 | 100 |
| 21 | 750 | 100 |

The invention claimed is:

1. A thiazole(bi)cycloalkylcarboxanilide of formula (I)

(I)

in which

Q represents a group

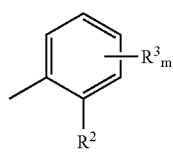

(Q-1)

$R^1$ represents hydrogen, $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, or $C_3$-$C_8$-cycloalkyl; represents $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, or $C_3$-$C_8$-halocycloalkyl having in each case 1 to 9 fluorine, chlorine and/or bromine atoms; or represents —$COR^7$, —$CONR^8R^9$, or —$CH_2NR^{10}R^{11}$, $R^2$ represents $C_3$-$C_{12}$-cycloalkyl, or $C_6$-$C_{12}$-bicycloalkyl, each of which is is optionally mono- or polysubstituted by identical or different substituents selected from the group consisting of halogen, cyano, hydroxyl, $C_1$-$C_8$-alkyl, $C_1$-$C_8$-alkoxy, $C_1$-$C_6$-haloalkyl having 1 to 9 fluorine, chlorine, and/or bromine atoms, and $C_1$-$C_6$-haloalkoxy having 1 to 9 fluorine, chlorine, and/or bromine atoms, $R^3$ represents fluorine, chlorine, bromine, or methyl, m represents 0, 1, 2, 3, or 4, $R^7$ represents hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; represents $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or represents 4-(difluoromethyl)-2-methyl-1,3-thiazol-2-yl, $R^8$ and $R^9$ independently of one another represent hydrogen, $C_1$-$C_8$-alkyl, $C_1$-$C_4$-alkoxy-$C_1$-$C_4$-alkyl, or $C_3$-$C_8$-cycloalkyl; or represents $C_1$-$C_8$-haloalkyl, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms, or $R^8$ and $R^9$ together with the nitrogen atom to which they are attached form a saturated heterocycle that is optionally mono- or polysubstituted by identical or different substituents selected from the group consisting of halogen and $C_1$-$C_4$-alkyl and that has 5 to 8 ring atoms, where the heterocycle optionally contains 1 or 2 further nonadjacent heteroatoms selected from the group consisting of oxygen, sulfur, and $NR^{13}$, $R^{10}$ and $R^{11}$ independently of one another represent hydrogen, $C_1$-$C_8$-alkyl, or $C_3$-$C_8$-cycloalkyl; or represent $C_1$-$C_8$-haloalkyl or $C_3$-$C_8$-halocycloalkyl having in each case 1 to 9 fluorine, chlorine, and/or bromine atoms, or $R^{10}$ and $R^{11}$ together with the nitrogen atom to which they are attached form a saturated heterocycle that is optionally mono- or polysubstituted by identical or different substituents selected from the group consisting of halogen and $C_1$-$C_4$-alkyl and that has 5 to 8 ring atoms, where the heterocycle optionally contains 1 or 2 further nonadjacent heteroatoms selected from the group consisting of oxygen, sulfur, and $NR^{13}$, and $R^{13}$ represents hydrogen or $C_1$-$C_6$-alkyl.

2. A thiazole(bi)cycloalkylcarboxanilide of formula (I) according to claim 1 in which
Q represents a group

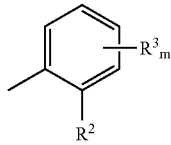

(Q-1)

$R^1$ represents hydrogen; $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, or $C_3$-$C_6$-cycloalkyl; represents $C_1$-$C_4$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_3$-alkoxy-$C_1$-$C_3$-alkyl, or $C_3$-$C_6$-halocycloalkyl having in each case 1 to 9 fluorine, chlorine, and/or bromine atoms; or represents —$COR^7$, —$CONR^8R^9$, or —$CH_2NR^{10}R^{11}$, $R^2$ represents $C_3$-$C_{12}$-cycloalkyl, or $C_6$-$C_{12}$-bicycloalkyl, each of which is optionally mono- to tetrasubstituted by identical or different substituents selected from the group consisting of fluorine, chlorine, bromine, cyano, hydroxyl, $C_1$-$C_6$-alkyl, $C_1$-$C_6$-alkoxy, $C_1$-$C_4$-haloalkyl having 1 to 9 fluorine, chlorine, and/or bromine atoms, and $C_1$-$C_4$-haloalkoxy having 1 to 9 fluorine, chlorine, and/or bromine atoms, $R^3$ represents fluorine, bromine or methyl, m represents 0, 1, 2, or 3, $R^7$ represents hydrogen, $C_1$-$C_6$-alkyl, $C_1$-$C_4$-alkoxy, $C_1$-$C_3$-alkoxy-$C_1$-$C_3$-alkyl, or $C_3$-$C_6$-cycloalkyl; represents $C_1$-$C_4$-haloalkyl, $C_1$-$C_4$-haloalkoxy, halo-$C_1$-$C_3$-alkoxy-$C_1$-$C_3$-alkyl, or $C_3$-$C_6$-halocycloalkyl having in each case 1 to 9 fluorine, chlorine, and/or bromine atoms; or represents 4-(difluoromethyl)-2-methyl-1,3-thiazol-2-yl, $R^8$ and $R^9$ independently of one another represent hydrogen, $C_1$-$C_6$-alkyl, $C_1$-$C_3$-alkoxy-$C_1$-$C_3$-alkyl, or $C_3$-$C_6$-cycloalkyl; or represents $C_1$-$C_4$-haloalkyl, halo-$C_1$-$C_3$-alkoxy-$C_1$-$C_3$-alkyl, or $C_3$-$C_6$-halocycloalkyl having in each case 1 to 9 fluorine, chlorine, and/or bromine atoms, or $R^8$ and $R^9$ together with the nitrogen atom to which they are attached form a saturated heterocycle that is optionally mono- to tetrasubstituted by identical or different substituents selected from the group consisting of halogen and $C_1$-$C_4$-alkyl and that has 5 to 8 ring atoms, where the heterocycle optionally contains 1 or 2 further nonadjacent heteroatoms selected from the group consisting of oxygen, sulfur, and $NR^{13}$, $R^{10}$ and $R^{11}$ independently of one another represent hydrogen, $C_1$-$C_6$-alkyl, or $C_3$-$C_6$-cycloalkyl; or represent $C_1$-$C_4$-haloalkyl or $C_3$-$C_6$-halocycloalkyl having in each case 1 to 9 fluorine, chlorine, and/or bromine atoms, or $R^{10}$ and $R^{11}$ together with the nitrogen atom to which they are attached form a saturated heterocycle that is optionally mono- or polysubstituted by identical or different substituents selected from the group consisting of halogen and $C_1$-$C_4$-alkyl and which has 5 to 8 ring atoms, where the heterocycle optionally contains 1 or 2 further nonadjacent heteroatoms selected from the group consisting of oxygen, sulfur, and $NR^{12}$, and $R^{13}$ represents hydrogen or $C_1$-$C_4$-alkyl.

3. A thiazole(bi)cycloalkylcarboxanilide of formula (I) according to claim 1 in which
Q represents a group

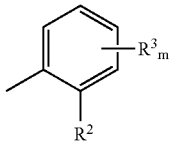

(Q-1)

$R^1$ represents hydrogen, methyl, ethyl, n- or isopropyl, n-, iso-, sec-, or tert-butyl, pentyl, or hexyl, methylsulfinyl, ethylsulfinyl, n- or isopropylsulfinyl, n-, iso-, sec-, or tert-butylsulfinyl, methylsulfonyl, ethylsulfonyl, n- or isopropylsulfonyl, n-, iso-, sec-, or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylsulfanyl, difluorochloromethylsulfanyl, trifluoromethylsulfanyl, trifluoromethylsulfinyl, trifluoromethylsulfonyl, or trifluoromethoxymethyl; or represents —$COR^7$, —$CONR^8R^9$, or —$CH_2NR^{10}R^{11}$, $R^2$ represents $C_3$-$C_{10}$-cycloalkyl, or $C_6$-$C_{10}$-bicycloalkyl, each of which is optionally mono- to trisubstituted by identical or different substituents selected from the group consisting of fluorine, chlorine, bromine, cyano, hydroxyl, methyl, ethyl, n- or isopropyl, n-, iso-, sec-, or tert-butyl, methoxy, ethoxy, n- or isopropoxy, n-, iso-, sec-, or tert-butoxy, trifluoromethyl, difluoromethyl, trichloromethyl, difluorochloromethyl, trifluoromethoxy, difluoromethoxy, trichloromethoxy, or difluorochloromethoxy, $R^3$ represents fluorine, bromine, or methyl, m represents 0, 1, 2, or 3, $R^7$ represents hydrogen, methyl, ethyl, n- or isopropyl, tert-butyl, methoxy, ethoxy, tert-butoxy, cyclopropyl; trifluoromethyl, trifluoromethoxy, or 4-(difluoromethyl)-2-methyl-1,3-thiazol-2-yl, $R^8$ and $R^9$ independently of one another represent hydrogen, methyl, ethyl, n- or isopropyl, n-, iso-, sec-, or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, or trifluoromethoxymethyl, or $R^8$ and $R^9$ together with the nitrogen atom to which they are attached form a saturated heterocycle selected from the group consisting of morpholine, thiomorpholine, and piperazine, each of which is optionally mono- to tetrasubstituted by identical or different substituents selected from the group consisting of fluorine, chlorine, bromine, and methyl, where the piperazine is optionally substituted on the second nitrogen atom by $R^{13}$, $R^{10}$ and $R^{11}$ independently of one another represent hydrogen, methyl, ethyl, n- or isopropyl, n-, iso-, sec-, or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, or trifluoromethoxymethyl, or $R^{10}$ and $R^{11}$ together with the nitrogen atom to which they are attached form a saturated heterocycle selected from the group consisting of morpholine, thiomorpholine, and piperazine, each of which is optionally mono- to tetra-substituted by identical or different substituents selected from the group consisting of fluorine, chlorine, bromine, and methyl, where the piperazine is optionally substituted on the second nitrogen atom by $R^{13}$, and
$R^{13}$ represents hydrogen, methyl, ethyl, n- or isopropyl, or n-, iso-, sec-, or tert-butyl.

4. A thiazole(bi)cycloalkylcarboxanilide of formula (I) according to any of claims 1, 2, or 3 in which $R^1$ is hydrogen.

5. A process for preparing a thiazole(bi)cycloalkylcarboxanilides of formula (I) according to claim 1 comprising (1) reacting a carboxylic acid derivative of formula (II)

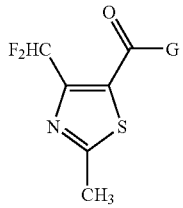
(II)

in which G represents halogen, hydroxyl. or $C_1$-$C_6$-alkoxy, with an aniline derivative of formula (III)

in which Q is as defined for formula (I) in claim 1, in the presence of an acid binder and in the presence of a diluent to form a compound of formula (I-a)

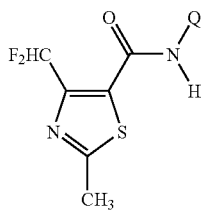
(I-a)

in which Q is as defined for formula (I) in claim 1, and (2) optionally reacting a compound of formula (I-a) with a halide of the formula (III)

$$R^{1-1}\text{—}X \qquad (IV)$$

in which $R^{1-1}$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, or $C_3$-$C_8$-cycloalkyl; represents $C_1$-$C_6$-haloalkyl, $C_1$-$C_4$-haloalkylsulfanyl, $C_1$-$C_4$-haloalkylsulfinyl, $C_1$-$C_4$-haloalkylsulfonyl, halo-$C_1$-$C_4$-alkoxy-$C_1$-$C_4$-alkyl, or $C_3$-$C_8$-halo-cycloalkyl having in each case 1 to 9 fluorine, chlorine, and/or bromine atoms; or represents —$COR^7$, —$CONR^8R^9$, or —$CH_2NR^{10}R^{11}$, $R^7$, $R^8$, $R^9$, $R^{10}$, and $R^{11}$ are as defined for formula (I) in claim 1, and X represents chlorine, bromine, or iodine, in the presence of a base and in the presence of a diluent.

6. A composition for eliminating or reducing unwanted microorganisms in plants comprising one or more thiazole (bi)cycloalkylcarboxanilides of formula (I) according to claim 1 and one or more extenders and/or surfactants.

7. A method for eliminating or reducing unwanted microorganisms in plants comprising applying an effective amount of one or more thiazole(bi)cycloalkylcarboxanilides of formula (I) according to claim 1 to the microorganisms and/or their habitat.

8. A process for preparing a composition for eliminating or reducing unwanted microorganisms in plants comprising mixing one or more thiazole(bi)cycloalkylcarboxanilides of the formula (I) according to claim 1 with one or more extenders and/or surfactants.

\* \* \* \* \*